United States Patent [19]

Stetter et al.

[11] Patent Number: 5,012,432
[45] Date of Patent: Apr. 30, 1991

[54] MICROCALORIMETER SENSOR FOR THE MEASUREMENT OF HEAT CONTENT OF NATURAL GAS

[75] Inventors: Joseph R. Stetter; Melvin W. Findlay, both of Naperville; Chongshan Yue, Chicago, all of Ill.

[73] Assignee: Gas Research Institute, Chicago, Ill.

[21] Appl. No.: 365,460

[22] Filed: Jun. 13, 1989

[51] Int. Cl.$^5$ ............................................. G01N 25/22
[52] U.S. Cl. .................................... 364/557; 374/37; 73/25.03; 364/571.01
[58] Field of Search ................... 364/557, 550, 571.01; 73/25, 26, 27 R, 27 A, 23.41, 23.42, 23.25, 25.01, 25.03, 23.31; 374/33, 36, 37; 422/52, 98, 94, 95, 51

[56] References Cited

U.S. PATENT DOCUMENTS

| | | | |
|---|---|---|---|
| 4,254,797 | 3/1981 | Mayeaux | 364/558 |
| 4,384,925 | 5/1983 | Stetter et al. | 364/571.01 |
| 4,464,925 | 8/1984 | Kolloff | 73/27 R |
| 4,492,480 | 1/1985 | Wadsö et al. | 374/33 |
| 4,533,520 | 8/1985 | Bossart et al. | 73/27 R |
| 4,541,988 | 9/1985 | Tozier et al. | 73/27 R |
| 4,614,721 | 9/1986 | Goldberg | 422/94 |
| 4,670,405 | 6/1987 | Stetter et al. | 422/98 |
| 4,731,226 | 3/1988 | Takahata et al. | 73/27 R |
| 4,854,155 | 8/1989 | Poli | 73/27 R |
| 4,870,025 | 9/1989 | Hurley et al. | 422/94 |

Primary Examiner—Parshotam S. Lall
Assistant Examiner—Michael Zanelli
Attorney, Agent, or Firm—Larson and Taylor

[57] ABSTRACT

The BTU content of a sample of natural gas is measured using a computer controlled microcalorimeter microsensor instrument employing a catalytic sensor. The instrument is portable for in field use and is able to obtain measurement accuracy of better than ±1%. A carrier gas, a standard reference gas and the sample gas to be measured are injected in a controlled manner through use of computer controlled solenoid valves and flow control valves, and a measurement loop injects precise gas volumes to enable a highly accurate BTU measurement by the catalytic sensor.

20 Claims, 8 Drawing Sheets

Fig. 1

(PRIOR ART)

MICROCALORIMETER SENSOR FOR THE MEASUREMENT OF HEAT CONTENT OF NATURAL GAS

BACKGROUND OF THE INVENTION

This invention relates to a gas BTU measurement apparatus and method, and more particularly, to the continuous measurement of the BTU content of natural gas using a microcalorimeter μ-sensor system.

The BTU content of natural gas typically varies between 900 and 1200 BTU/Ft$^3$. Methane content can range from a low of 80% up to close to 100%. Precise measurement of the BTU content of natural gas is extremely important in a wide variety of applications. Current methods are time consuming and use expensive equipment. A simple, low-cost, and reliable microsensor (μ-sensor) that can measure the BTU content of a hydrocarbon stream with high accuracy is highly desirable.

Figure 1:
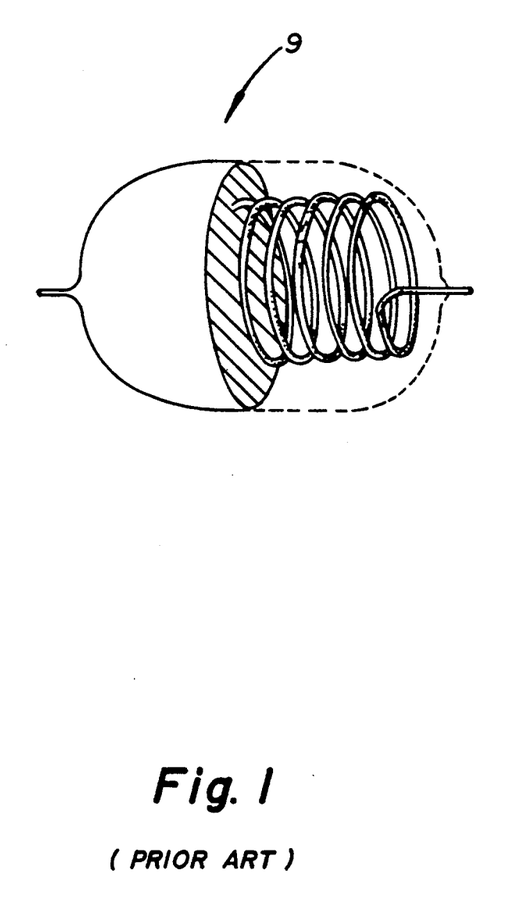
FIG. 1 is a perspective view of a typical combustible gas sensor bead consisting of a catalyst coated platinum (Pt) wire.

Gas sensors for the measurement of the lower explosion limit of combustible gases like methane (such as in safety alarm devices, also called flammable gas alarms) have been available for many years. Most of the modern combustible gas sensors are built like tiny heterogeneous catalytic reactors. A schematic of such a combustible gas sensor is shown in FIG. 1. The sensor consists of a coil of fine platinum (Pt) wire over which a catalyst (Pt on alumina) bead has been formed. The overall dimensions of the bead can be much less than a mm$^3$ making it a very small sensor indeed.

In such gas sensors, the bead is heated by passing a current through the platinum wire. Any combustible gas that comes into contact with the hot catalyst on the bead surface reacts according to equation 1 below (a similar reaction can be written for any hydrocarbon), producing some heat, denoted dH. The amount of heat produced is proportional to the heat of combustion of the hydrocarbon and the number of molecules reacting (concentration).

$$CH_4 + 2\ O_2 = CO_2 + 2\ H_2O + dH \quad (1)$$

or more generally $$a\ [HC] + b\ O_2 = c\ CO_2 + d\ H_2O + dH \quad (2)$$

The platinum wire in the sensor is also a resistance thermometer, i.e., its resistance changes with temperature. Some of the heat (dH) from the combustible gas reaction at the catalyst surface is lost by conduction, convection, and radiation, while some part of the dH goes into the catalyst bead causing an increase in bead temperature ($dH = C_p\ dT$). The change in bead temperature, in turn, causes a change in resistance of the sensor's Pt wire. The change in resistance of the Pt wire is typically monitored by placing the bead in a Wheatstone bridge circuit with a compensating element (passivated and matched) and two known resistors. Small changes in temperature corresponding to a few hundred to a few thousand ppm of $CH_4$ can be detected as an imbalance in the resistance bridge circuit. This relationship is usually expressed as $$S = K\ dH\ [CH_4] \quad (3)$$

where S is the "signal" from the sensor (corresponding to the imbalance in the bridge in volts) and K is an instrument constant that is obtained by calibration of the sensor with a known concentration of methane in air.

The signal from combustible gas sensors wherein the gas concentration is measured is typically linear over the range 0–5% methane for some sensors and linear up to 10% methane for others. Because the sensor is operated in a diffusion limited region, the signal is proportional to the amount of gas reaching the bead.

Since the total amount of gas diffusing to the bead is constant, the output signal depends upon the relative amount of methane in the sample. The constant, K, depends upon the type of gas, i.e., methane, ethane, or propane, being detected (i.e., different gases cause a different temperature rise) and the sensor housing design (the geometry of the device). The value of the constant K varies with the type of gas for two reasons: (1) different gases have different heat content and therefore produce more or less heat upon combustion, and thus produce more or less of a temperature rise to be transduced from a thermal into an electrical signal, and (2) the calorimetric or heat transfer properties of the bead and gas can change from bead to bead, from gas to gas, and from method to method.

As discussed below, one aspect of the present invention concerns the use of microprocessor control for injection of a gas sample. When samples are injected manually, this necessarily involves a start and stop procedure. The results therefore, are never as precise as a computer controlled system. A computer operating, for example, with a 1 microsecond sampling time is able to perform operations with a theoretical precision in the order of one part in a million. Further, computer control will cause a switch (a solenoid control valve for the controlled injection of a sample) to always have a constant response time, e.g. 3 millisecond. Hence, the flow perturbations, pressure perturbations and temperature perturbations that are introduced by these fast operations are practically nil, and cannot be sensed by a sensor.

To the contrary, in a manually operated system, performing a function may take a couple of seconds, for example, which introduces fluctuations large enough that they would disturb the measuring system so that error is introduced.

Calorimeters are currently available, such as ones manufactured by Cutler-Hammer, that measure BTU content to a high degree of precision, such as in the <1% range. These devices, however, are expensive, costing around $30,000, use a flame rather than a catalytic sensor, and do not have the portability that is highly desired. No devices presently known in the art use a catalytic sensor to produce BTU measurement with accuracies <1%, and provide convenient portability, at low production cost.

SUMMARY OF THE INVENTION

Generally speaking, the present invention utilizes a catalyst bead sensor such as described above as a component of a sensor device for measuring the heat content of a gas. The resultant sensor device is portable and substantially less expensive than prior art calorimeter devices while at the same time provides a very high degree of measurement precision.

The invention is based in part on an appreciation from the theory underlying the catalyst bead device illustrated in FIG. 1 that (a) if a measurement can be made of concentration by the amount of heat given off, then (b) a measurement should be able to be made of heat (dH) given off for a given concentration. In other words, the device can be used as a basis for a sensor to either (a) determine a sample concentration as a function of heat content or (b) to measure heats of combustion (a calorimeter) as a function of concentration of the sample.

The present invention uses the heat transfer properties of the catalyst bead to provide BTU measurement. In an important embodiment, the catalyst bead is operated at constant power input and the hydrocarbon reaction (equation 1) is diffusion limited. A diffusion limited reaction occurs by using an active catalyst that reacts every molecule reaching the surface. The traditional combustible gas sensor operates in this manner (diffusion limited) and in the present invention the amount of gas reaching the surface is kept small by dilution of the sample.

In accordance with the invention, a catalyst bead is housed in a small system volume with a constant flow carrier gas into which a small injection of a gas sample is made. For purposes of analysis, let us assume the device operates at constant temperature. Under these conditions, the energy balance of the catalyst is examined as follows. The power required to keep the catalyst bead at a constant temperature is the electric work (amps × volts) put into the bead, i.e., the power, P. This is exactly balanced by the heat loss of the bead by radiation, convection, and conduction. If the combustible gas sample comes to the bead and reacts, it will deposit some fraction of its thermal energy or heat (=alpha, $\alpha$, dH) for each molecule reacting. This added heat will reduce the electrical power, P, required to keep the catalyst bead at the same (constant) temperature to a new value, P'.

The energy balance for the bead can be expressed as:

$$P = P' + \alpha\, dH\, (dn/dt) \tag{4}$$

where dn/dt is the rate of reaction and, $$dP = P - P' = \alpha\, dH\, (dn/dt) \tag{5}$$

If the system is operated at constant temperature and at steady-state in dilute solutions, changes in the calorimeter response due to thermal properties of the products and reactants will be minimized. Equations 4 and 5 indicate that the difference in power (dP) will be proportional to the heat (dH) at constant reaction rate, dn/dt. The reaction rate at constant temperature is only a function of the concentration (dn/dt=k [HC]). This result is the same as the empirical observation made in equation 3. The sensor is easily calibrated with a substance of known dH and known concentration to obtain the constant alpha, $\alpha$. Subsequent measurements on samples of unknown heat content are used to determine dH for each sample.

The thermodynamic energy balance considerations establish the fact that either (a) dH can be determined as a function of dn/dt (concentration), or (b) concentration can be determined as a function of dH (or substance) using the sensor bead power requirement as a response.

The power requirement of the bead is measured by monitoring the current I and voltage V being supplied to the bead by conventional electronic techniques. It is important to remember that absolute values are not as important as being able to measure differences in I and/or V with high precision for any practical calorimeter.

Since dH is to be determined with the proposed sensor application, the $\mu$ sensor system is operated at a constant amount of injected sample gas, or in other words, with a constant concentration in the gas stream of sample gas being fed to the sensor. The observed signal, dP, is proportional to the heat content, dH, of the gas sample which, in turn, is proportional to the total amount of hydrocarbon in the injected sample. Comparison of signals for known samples provides a calibration of the system (numbers for $\alpha$ dn/dt similar to any classical calorimeter constant so that the device can be used with unknowns.

The system can be operated with the sensor bead maintained at either constant temperature, assuming the emissivity and system heat losses are constant, or at constant voltage. It is much easier to operate the bead at a constant voltage and use the resistance change upon small changes in temperature, dT, as the signal. These resistance changes can be measured very accurately using a Wheatstone bridge. The dT can be a precise measure of the concentration and is the method typically applied in combustible gas meters available commercially.

To examine the non-isothermal operation of the catalytic sensor device is useful. The thermodynamic considerations involve equating power input P(T), which is the heat being lost at steady state, plus the heat generated by the sample combustion on the bead to the new power loss of the bead at the elevated temperature, P'(T), plus the heat needed to raise the temperature of the sensor bead (Cp dT/dt) to this new temperature. The equations are a bit more complex because the power required to keep the catalyst bead at a higher temperature is a function of temperature (i.e., the rate of heat emission from the surface changes with temperature but this can be part of the instrument calibration). If the power to the bead is kept constant and the temperature allowed to change:

$$C_p\, (dT/dt) = P(T) + \alpha\, dH\, (dn/dt) - P'(T) \tag{6}$$

where $$P'(T) = P(T1) - P(T2) \text{ and } P(T1) = P(T) \tag{7}$$

and, at steady-state $dT/dt = 0$ so that $$-P(T2) = \alpha\, dH\, (dn/dt) \tag{8}$$

and $P'(T2) = dT[\delta P/\delta T]$ for small changes to the signal (the change in the catalyst bead temperature and composition) and then the change in temperature, dT, may be expressed as:

$$dT = \frac{\alpha\, dH\, (dn/dt)}{-(\delta P/\delta T)} \tag{9}$$

Equation (9) suggests that the change in temperature can be related to the heat (dH) at constant concentration also. The constant $[\alpha/\delta P/\delta T)]$ is found in the usual manner by calibration with gases of known heat constant. The constant $\delta P/\delta T$ is the catalyst bead's ability to dissipate heat (by radiation, convection, and conduction). Equation (9) is important because it implies that the sensitivity of the microsensor microcalorimeter will be a maximum when $\alpha$ is maximum (i.e. there is maximum heat transfer by reaction) and when ($\delta P/\delta T$) is minimum (i.e., there is minimum heat loss by the calorimeter). In other words, the more heat transferred to the microcalorimeter (high $\alpha$), the larger the change in temperature ($dT = dH/Cp$).

The temperature change mode of operation, i.e. maintaining voltage constant, is the normal operation mode for catalytic combustible gas devices, and is one approach used in the preferred embodiment of the invention.

The conclusion to be made from the thermodynamic analysis described above is that it is possible to determine dH of unknown samples with the catalyst microcalorimeter sensor. The use of this approach requires a microsensor catalyst that functions as a microcalorimeter instead of a concentration meter. This is accomplished according to the invention by using a carefully controlled sample injection and dilution system.

In order to get a signal proportional to the heat of combustion, calibration with a known gas and concentration is important. This calibration process is no different than that required for any sensor or analytical method including current calorimetric and GC methods. However, calibration of the microsensor bead will be much faster and simpler.

The above simple energy balance (thermodynamic model) leads to the conclusion that it is feasible to obtain signals from the disclosed device that can measure the BTU content of an unknown gas stream. The simplest operation is to inject a constant amount of sample, dilute to the concentration region wherein the microcatalyst operates, and then detect the change in temperature (signal) produced by gases with differing heat content.

The constant (power/dt) measurement has been found to be accurate over narrow ranges of temperature. The magnitude of temperature change is controlled by controlling the size of the sample injected into the gas stream (dilution).

For application where larger amounts of heat are to be measured, it may be desireable to use the more complicated constant temperature/$\Delta$ power measurement described below.

A distinctive feature of the invention is its high precision, yielding a degree of accuracy in measuring BTU content to <1%.

DETAILED DESCRIPTION OF THE PREFERRED EMBODIMENT

Figure 2:
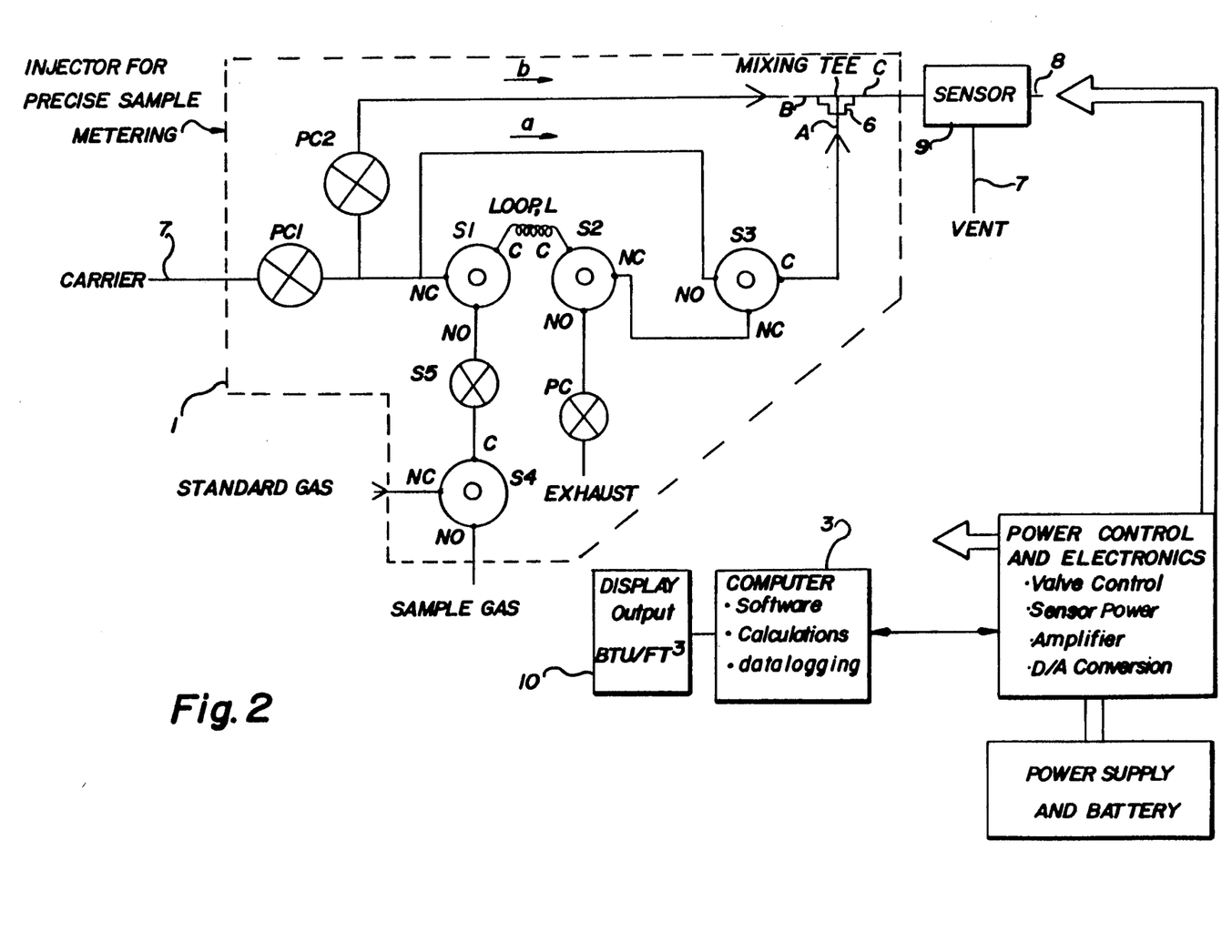
FIG. 2 is a schematic block diagram of a BTU measuring instrument according to the invention.

Referring now to FIG. 2, a gas BTU measuring instrument is depicted with the injector system 1 of the instrument shown within the broken lines. As is described in more detail below, the injector operation is controlled by computer 3 using a measured loop for precise gas metering. In a preferred embodiment, there are two flowing gas streams, a carrier (or dilution) gas and a sample gas. The carrier gas merges with sample gas at a mixing tee 6.

The sample gas loop injection system always introduces a precise amount of gas, e.g. 5 cc, 3 cc, or 1.004 cc, according to design choice, whether it is a standard gas for calibration or a sample gas for measurement. It is important that the sampling system always injects precisely the same amount. It is the coupling of this precise metered amount of sample in a precisely controlled, constant flowing gas stream, diluted in a precisely constant dilution with a carrier gas stream that produces a desired range of signals so that a very precise and accurate measurement of the heat value is obtained.

It should be understood that such precision is not available with the bead by itself. Moreover, as discussed above, in the known art, the sensor bead is used basically by itself to measure concentration. Such a sensor bead has heretofore not been used to measure the heat content (BTU) of a gas. Further, no single present method of measuring heat content controls all of the critical factors, such as concentration, flow rate, temperature, pressure power and other variables as are controlled in the present invention, to make a heat measurement. As discussed above, it is for this reason that prior to the present invention, there has been an inability to measure the heat content of a gas accurately and at a reasonable cost in a portable instrument because such measurement has not been coupled with an accurate flow system as described below.

The instrument is calibrated by inputting a standard (or reference) gas of known BTU content, i.e. heat value, into the instrument, with the normally closed (NC) terminal of a solenoid valve S4 opened by computer 3. This allows the standard gas to be injected through a solenoid valve S1 into loop L in preparing the loop for injection.

The standard is controlled to proceed through solenoids S2 and S3 into input A of mixing tee 6 where it meets with a carrier gas.

The carrier or dilution gas is supplied to the instrument at input 7 and proceeds through a flow control valve FC1. A further flow control valve FC2 controls the ratio of flow "a" through the standard gas line to a first input A of tee 6 and the flow "b" through the diluent line to a second input B of tee 6. The standard gas is diluted by the diluent or carrier gas, and the resultant mixture flows out of output C of mixing tee 6 downstream to sensor 9 incorporating a sensor bead such as that shown in FIG. 1.

The diluent gas must contain oxygen for the combustion process. This oxygen can be oxygen in air or pure oxygen. The air used should generally be clean and not contain a high level of impurities. It is important that the amount of air be constant. For example, room air could not be used since one time it might have only a small amount of contamination, the next time a great deal. The diluent gas could contain a small amount of hydrocarbon so long as the content thereof is constant.

The sensor bead itself of sensor 9 is suspended in the diluted gas flow. When the carrier gas flows by the bead, no unusual signal is produced by sensor 9. Stated differently, the head of sensor 9 exhibits a constant resistance throughout the flow of the carrier gas thereby. However, when a mixture of carrier and standard gases are caused to flow by sensor 9, a portion of the standard gas reacts with the bead surface, i.e. the surface is catalytically oxidized. The reaction that occurs on the bead surface generates heat, which changes the temperature of the bead. The change in temperature causes a change in the bead resistivity. Since the bead is a component in an electronic circuit, a Wheatstone Bridge for example, this change in resistance produces an output signal due to an imbalance in the bridge. This signal produced by sensor 9 is used as a measure of the amount of heat being generated.

As stated above, when only a carrier flows by sensor 9, there is no signal produced. This is reflected in a straight baseline signal as shown in dashed lines in FIG. 3(b). As soon as a second gas (either a standard or a sample) is introduced to sensor 9, an excursion from the baseline occurs in the sensor output signal and that excursion is a measure of the BTU concentration of the second gas.

Figures 3A, 3B:
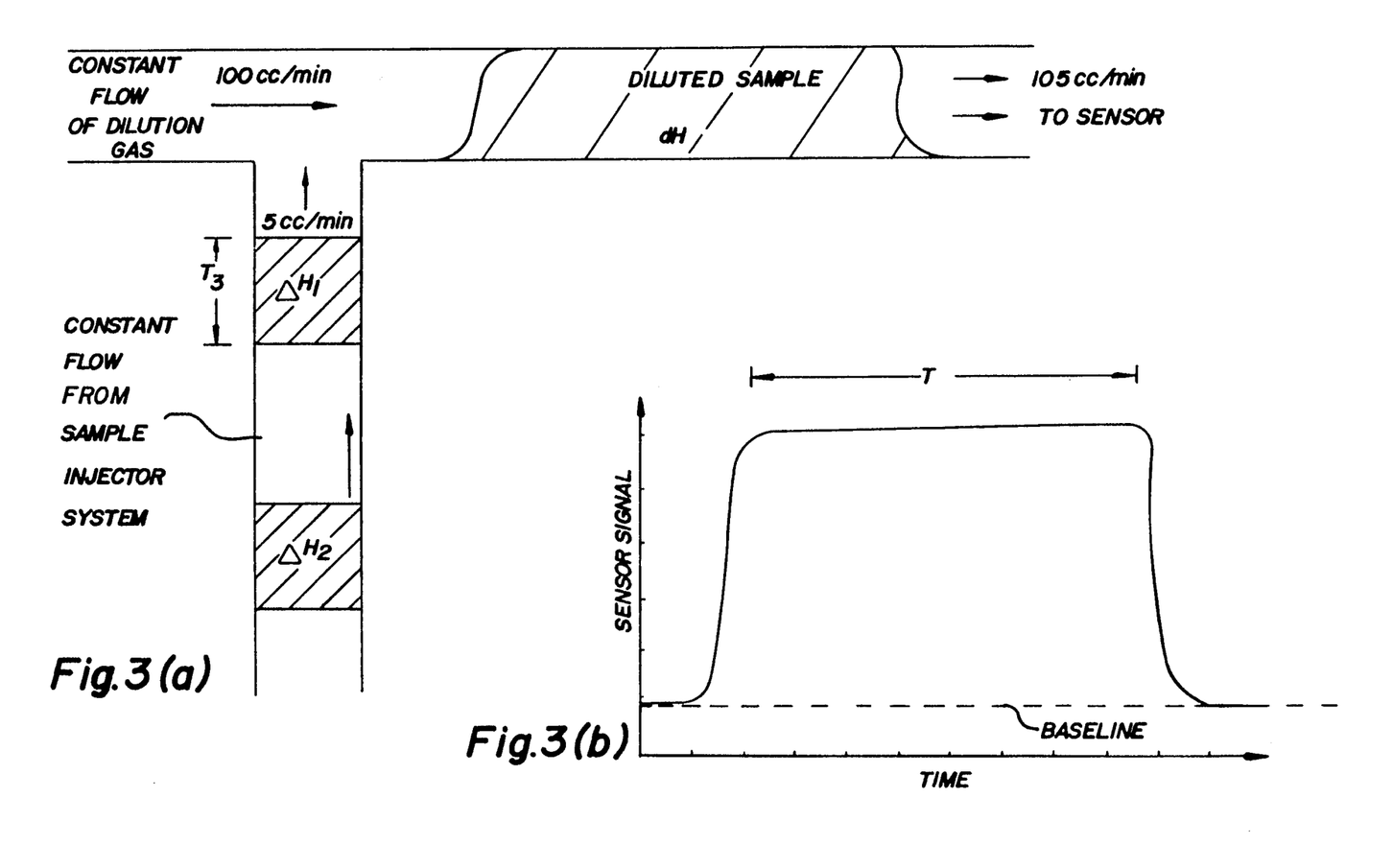
FIG. 3(a) is a diagram illustrating the dynamics of a flow system at a mixing tee shown in FIG. 2.
FIG. 3(b) is a graph of measurement cycle showing the sensor signal vs. time of a diluted sample corresponding to the flow position of the diluted sample.

If this procedure is first carried out using a standard gas, e.g. one that is known to have 1,000 BTUs/ft.$^3$, the excursion peak of FIG. 3(b) would show 1,000 units (relative sensor signal strength). The sample gas is then injected into the system in place of the standard gas. If the sample gas, for example, produces an excursion of 900 units, then it is known that the sample gas has nine-tenths of the heating value of the standard gas.

Three methods are possible for use in calculating the BTU content of the sample gas from the obtained data. The preferred method is to use a ratio of the excursion of the sample to the excursion of the standard, according to the following formula:

$$(BTU)_{SAMP} = \left[\frac{S_{SAMP}}{S_{STD}}\right](BTU)_{STD} \cdot C_1 + C_2$$

where
 $C_1$ = slope
 $C_2$ = intercept

The two other methods involve use of peak area and/or of multiple standards in calibrating the BTU content value. The peak area approach makes use of the following formula:

$$(BTU)_{SAMP} = \left[\frac{A_S}{A_R}\right](BTU)_{STD} \cdot C_1 + C_2$$

where $A_S$ = area under the curve of sample
$A_R$ = area under the curve of standard Thirdly, applying the method of using more than one reference will serve to widen the range of accuracy of the measurement.

Figure 6A:
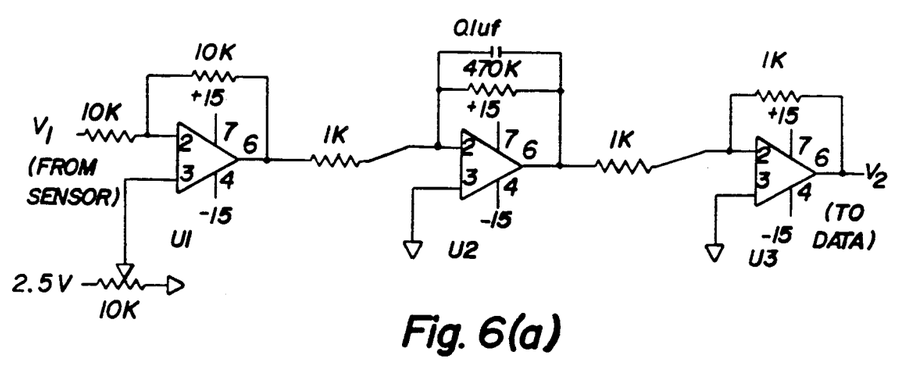
FIG. 6(a) is a schematic circuit diagram of a signal amplifier and measurement circuit that is connected to the output of the catalytic sensor and to a computer data acquisition input and is incorporated in the power control and electronics module of FIG. 2.

Operation of the system could be carried out with the bead maintained at constant power, or maintained at constant voltage. The preferred embodiment uses constant voltage as a simpler way to carry out the measurement. At constant voltage, the bead temperature will change, but the temperature excursions are small because the sample is diluted. The small excursions are enlarged electronically for analysis using an amplifier circuit (as shown in FIG. 6(a)), which controls the amplitude so that the excursions are not so large as to otherwise cause large inaccuracies in the measurement. Changes in bead temperature produce a change in its resistance which can be measured, e.g., in a Wheatstone Bridge circuit. The amount of the resistance change is proportional to the BTU content of the gas.

Another approach that produces the same degree of a accuracy is to conduct the measurement maintaining a constant power to the bead sensor.

The "vent" 7 of the sensor 9 of FIG. 2 forms a final output for the gas flow from the measuring instrument. Typically, the system is vented directly to the atmosphere, where its operation then assumes atmospheric pressure, which can change daily with the barometric reading. A desirable option is to install a pressure regulator at the vent output to raise the system somewhat above atmospheric pressure and have it operate at a constant pressure for even greater accuracy.

The power control and electronics module 12 performs all electronic operations of the system, e.g. controls switching of the flow control valves and the solenoid valves in the operation of the sensor.

The display 10 of FIG. 2 displays the output data in terms of BTU/ft.3 However, an operator can program the computer 3 to display any number of variations in the output data as desired.

Figure 6B:
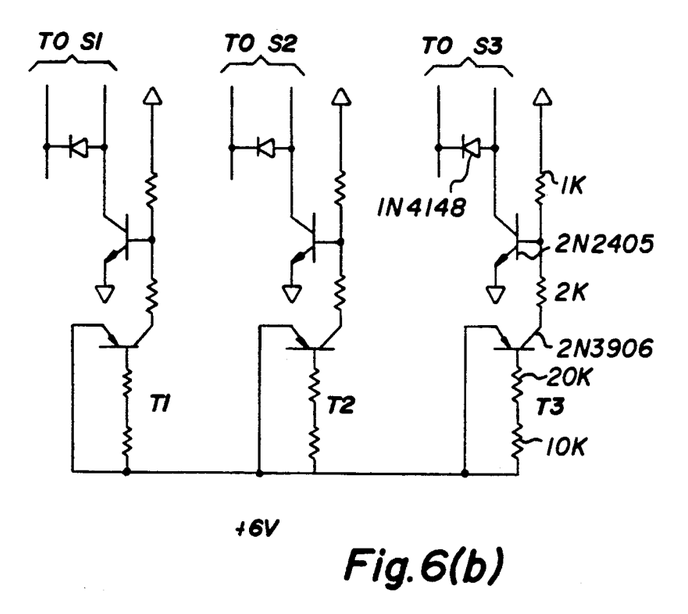
FIG. 6(b) is a schematic circuit diagram of a basic solenoid driver circuit illustrated for the solenoid valves of FIG. 2 and is incorporated in the power control and electronic module of FIG. 2.

FIG. 6(b) shows circuitry used to power the solenoid valves of FIG. 2. The individual circuits are, as shown, replicas of one another. Although illustrated for only solenoid valves S1, S2 and S3, the circuitry for solenoid valves S4, S5, etc. would also be the same.

The circuits of FIGS. 5(a) and 5(b) and 6(a) and 6(b) are part of the power control module 12 of FIG. 2.

Figure 5A:
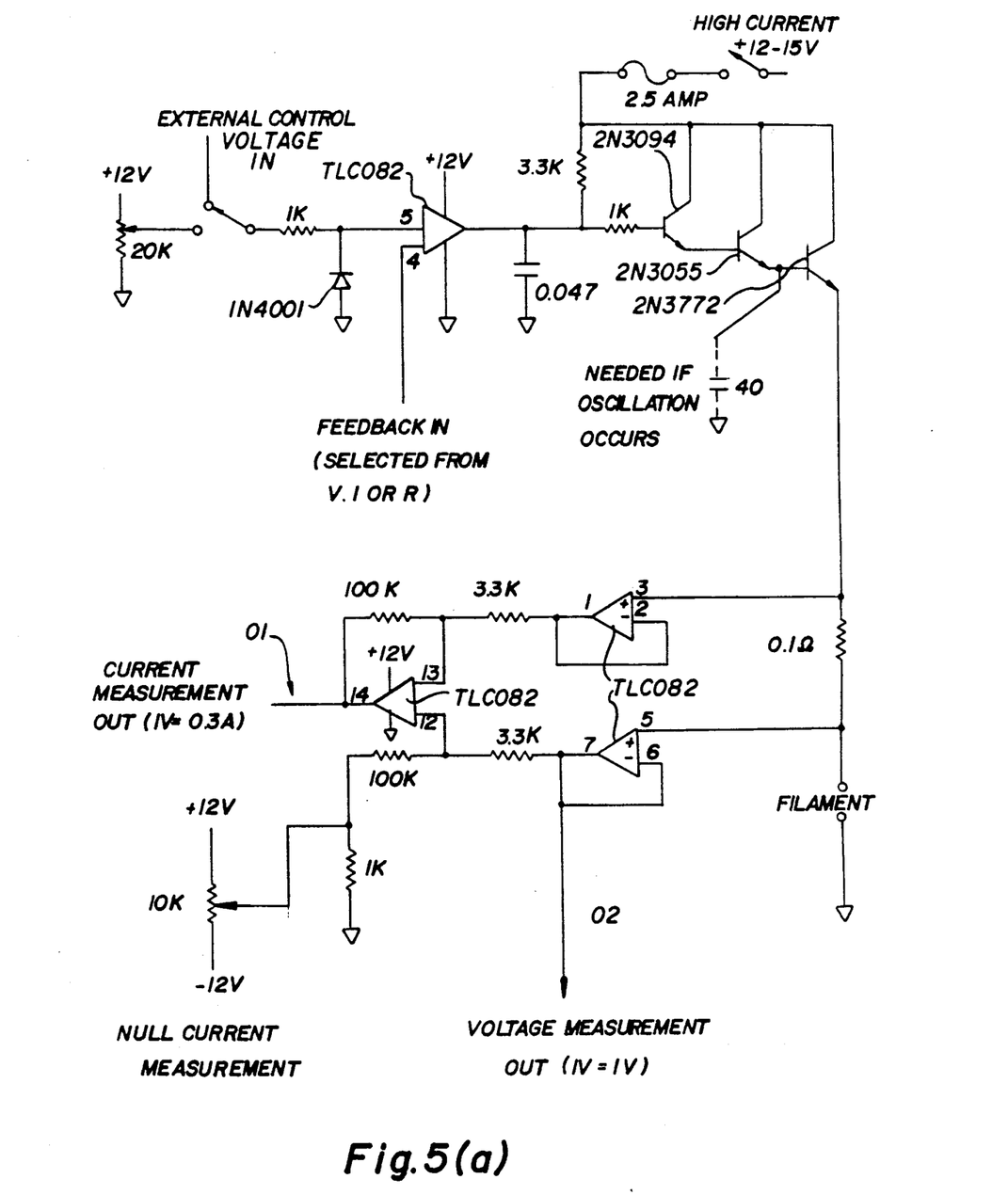
FIG. 5(a) is a schematic circuit diagram of a filament controller providing voltage and current measurements incorporated in the power control and electronics module of FIG. 2.
Figure 5B:
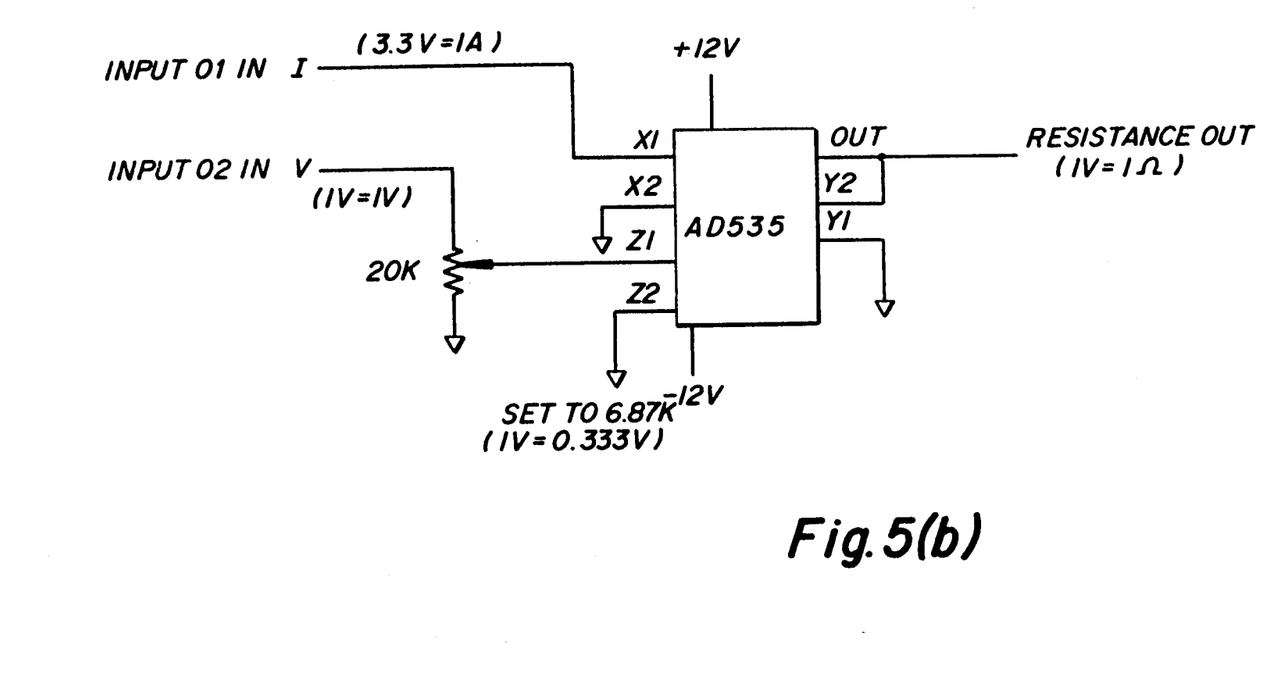
FIG. 5(b) is a schematic circuit diagram used in calculating filament resistance and incorporated in the power control electronics module of FIG. 2.

FIGS. 5(a) and 5(b) show circuitry used when that sensor bead is kept at a constant temperature, and the variation in power required to maintain that constant temperature is measured. Since the variable signal is a change in power, not a change in temperature, the voltage change is measured, such as by means of a voltage comparator circuit where two voltages are compared and the output is proportional to the comparison. If the temperature is used as the variable, a measuring circuit such as a Wheatstone Bridge would be used to measure the change in resistance.

As stated, an accurate dilution of the sample is a crucial step in obtaining a high accuracy measurement. This precise dilution has been described as being accomplished by use of a pressure regulated flow stream. There are other ways to provide accurate dilution of the sample including, for example, using critical orifice technology, or semi-permeable membrane technology, as are known to those skilled in the art.

Figure 4A:
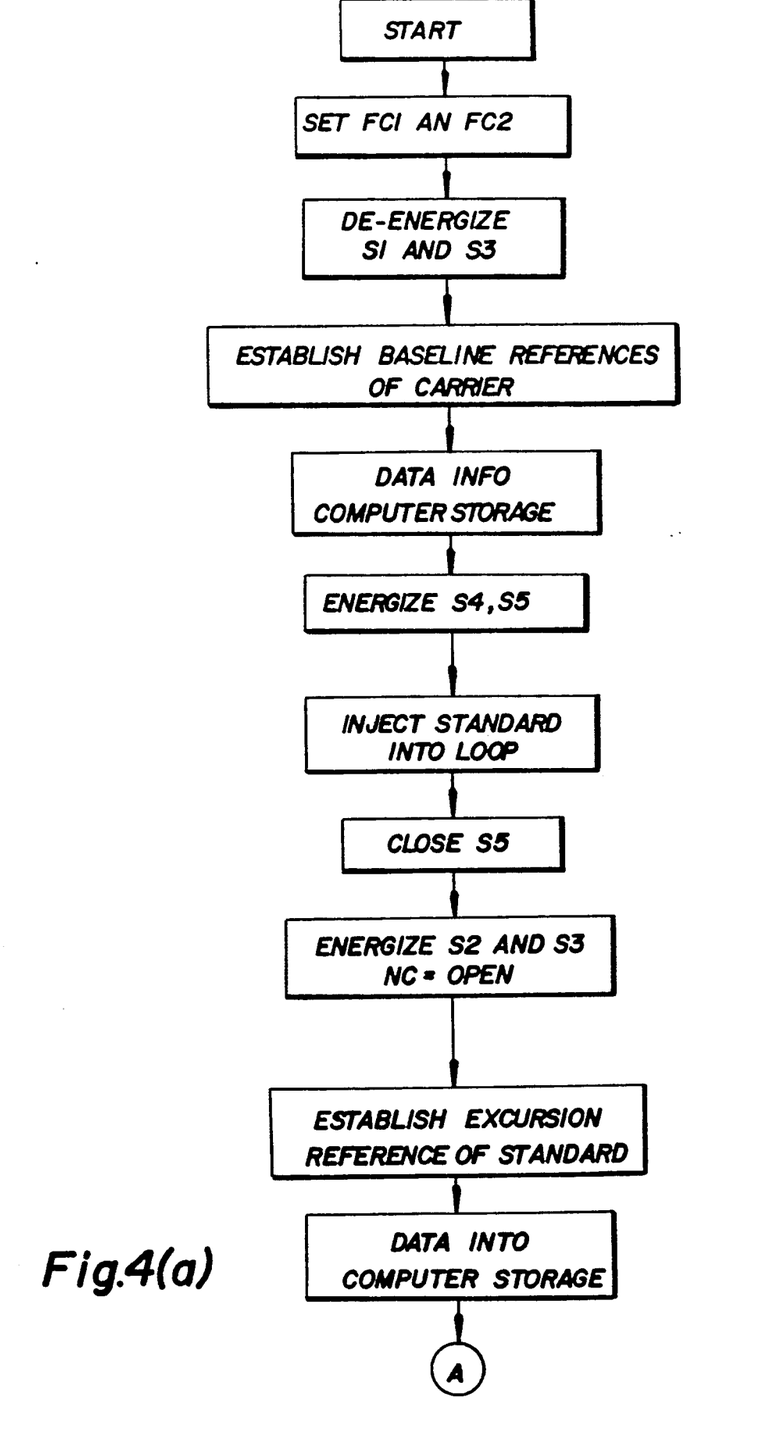
FIGS. 4(a) and (b) is a flow chart showing the steps involved in carrying out the measurement of BTU content of a sample gas according to the invention.
Figure 4B:
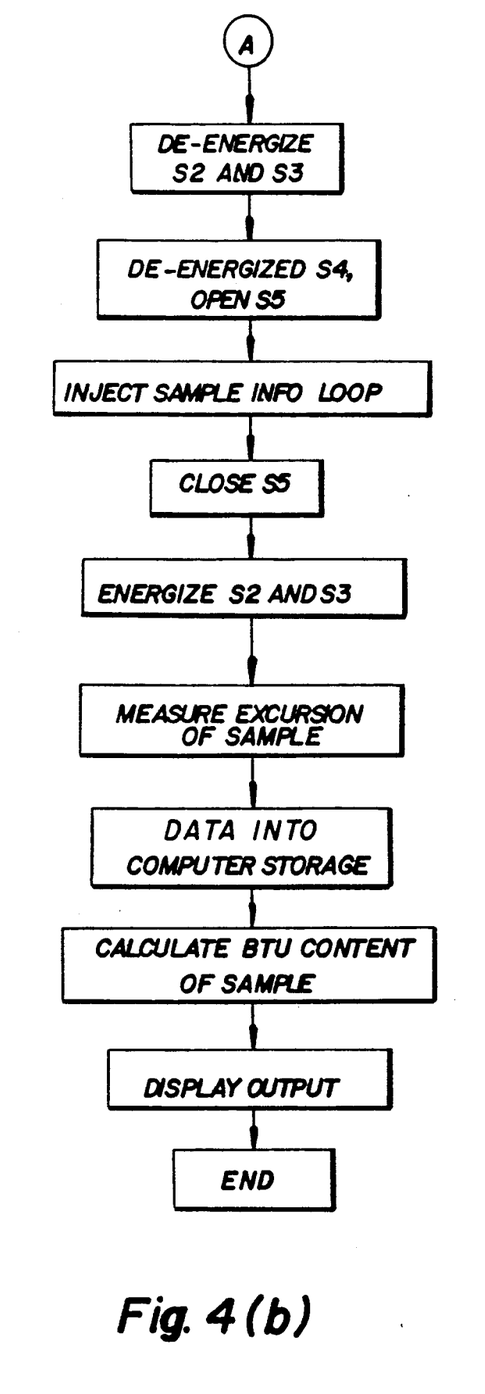

The method according to the invention will now be discussed with reference to the flow diagram of FIG. 4 in conjunction with the apparatus of FIG. 2.

Flow control valves FC1, FC2 are set by computer 3 to establish a predetermined rate of carrier gas flow in the system. The ratio of sample flow in path "a" to diluent flow in path "b" is determined using valve FC2. This is also the first step in obtaining a baseline reference for the sensor signal (see FIG. 3(b)). Solenoid valves S1 and S3 are in their de-energized states so that carrier gas flows along path "a", bypassing the loop L, and along path "b", being split therebetween according to settings of valves FC1 and FC2. At tee 6 the paths merge and the carrier gas proceeds to flow past the sensor 9 and out of vent port 7.

Monitoring the sensor signal output terminal 8 of the catalytic sensor 9 establishes a baseline reference as indicated by the dashed line of FIG. 3(b). Data from the sensor output is placed into computer storage.

Next, the loop L shown in FIG. 2 is filled with a standard gas, i.e. one the BTU content of which is known, by energizing solenoid valves S4, S5. Once loop L is filled, valve S5 is closed, and solenoid valves S1, S2 and S3 are energized so that carrier gas flowing through valve S1 causes the standard gas to be expelled from the loop L, and flow through solenoid valves S2 and S3, and into mixing tee 6. In tee 6 the standard gas mixes with the carrier gas, in precise amounts as controlled by computer 3. The gas mixture flows from tee 6 downstream past sensor bead 9. Contact by the sensor with the predetermined amount of standard gas in the gas mixture causes an excursion of the sensor signal from the baseline as shown in FIG. 3(b). This excursion corresponds in time with the flow of the diluted standard gas sample through the system, as illustrated by the relationship shown in FIGS. 3(a) and 3(b). The excursion of the standard gas is measured, and this data is also placed into computer storage. Solenoid valves S2 and S3 are returned to their normal conditions.

A similar procedure is then carried out using the sample gas to be measured instead of a standard gas. Valve S4 is de-energized and valve S5 energized to allow loop L to be filled with sample gas. Solenoid valve S5 is then closed, and valves S1, S2 and S3 are energized so that the carrier gas expels the sample gas from the loop L and the sample gas flows into mixing tee 6. The sample gas mixes with the carrier gas in tee 6 and the mixture flows past sensor 9 downstream. In the same manner as with the standard gas, the excursion of the sensor signal caused by the presence of known amount of sample gas is measured, and the data placed into computer storage.

The computer 3 uses the data in storage therein to calculate the BTU content of the sample gas, and that figure is displayed by display 10. It will be understood that various types of output displays may be used, that various data can be presented and format of the output display selected as desired.

The computerized system can later be used to perform the next analysis by repeating basically the same procedure of establishing a baseline reference of the carrier gas, calibrating the system using a standard gas having a known BTU content, and using this information in conjunction with data obtained from a sample gas to determine the BTU content of the sample gas. It will be understood, of course, that once the system is calibrated it is normally unnecessary to recalibrate the system where, for example, a number of gas samples are supplied to the system in sequence, i.e. at substantially the same time.

Variations of the procedure discussed above include the use of two measured loops to allow faster analysis of standard and sample, or the use of two loops and two matched sensors, to allow for the simultaneous analysis of standard (reference) and sample gases.

The power control and electronics module 12 shown in FIG. 2 also provides power for the operation of the overall system, including computer 3, the valve controls, the sensor 9, and related electronic circuitry incorporated in the module such as amplifiers and D/A convertors. The power control portion is designed to be used with a portable power supply and, in particular, with a power supply and battery unit 13, so the resultant instrument is portable and usable in field test conditions. The computer 3, which may include a programmable microprocessor, provides data calculations and carries out the computer-controlled operation of various components of the system, and in particular, the solenoid valves, flow control valves and pressure controller of the injector system.

Referring again to FIGS. 5(a) and 5(b) as stated, the, circuitry shown is for use in maintaining the sensor 9 at a constant temperature by varying the power inputted to the sensor 9. FIG. 5(a) shows a filament controller where current is measured at output $O_1$ by means of a voltmeter using the conversion factor of 1 volt=0.3 amps. Voltage out is measured at $O_2$ by a voltmeter applying a unity conversion, i.e. one volt=one volt. The outputs of $O_1$ and $O_2$ of FIG. 5(a) are shown as the two inputs to the circuit of FIG. 5(b) for calculating filament resistance from these voltage and current measurements. Thus, by measuring the change in power necessary to maintain a constant sensor bead temperature provides a method for calculating the bead filament resistance.

FIGS. 6(a) and (b) show representative circuitry used to carry out the operation of the apparatus. FIG. 6(a) illustrates circuitry connected to the output of the sensor 9 for processing the signal produced by sensor 9 for input to a data acquisition input of computer 3. As noted above, FIG. 6(b) depicts the basic solenoid driver circuitry, shown as replications of the same circuit for solenoid valves S1, S2 and S3. Similar additional circuitry would simply be added for additional solenoid valves, such as solenoid valves S4, S5.

With this detailed description of specific apparatus and circuitry used t illustrate the preferred embodiment of the present invention and the operation thereof, it will be obvious to those skilled in the art that various modifications can be made in the gas BTU content measuring apparatus disclosed, and the means for implementing the method and apparatus of the present invention, without departing from the spirit and scope of the present invention.

What is claimed is:

1. An apparatus for measuring the BTU content of a sample gas, said apparatus comprising,
    a catalytic sensor means for sensing the heat content of a gas,
    processing means operatively associated with said sensor means for calculating and display means for displaying the heat content of gas in contact with said sensor,
    first flow control means for providing a predetermined flow of a carrier gas into contact with said sensor means for establishing and storing a baseline reference signal of heat content of the carrier gas in said processing means, second flow control means having measuring means therein for providing a precise gas volume chamber and valve means connected with said measuring means whereby a standard gas is injected into said measuring means to provide a metered sample of standard gas, said second flow control means including means for mixing the metered sample of standard gas with carrier gas and for passing the sample of standard gas and carrier gas into contact with the sensor means to provide and store a further reference signal of heat content in said processing means, and whereby a sample gas is subsequently injected into said measuring means to provide a metered sample of sample gas to be mixed with carrier gas and the mixed sample gas and carrier gas passed into contact with the sensor means to provide a signal to enable said processing means to calculate the heat content of the sample gas.

2. An apparatus according to claim 1, wherein the measuring means comprises at least one calibrated loop for measuring out a precise predetermined amount of gas.

3. An apparatus according to claim 1, wherein said sensor means comprises a catalytic, flameless sensor.

4. An apparatus according to claim 1, wherein said sensor means comprises a sensor maintained at constant power.

5. An apparatus according to claim 1 wherein said sensor means comprises a sensor maintained at constant temperature.

6. An apparatus according to claim 1, wherein the sensor means includes vent means for expelling gas at an output of the sensor means.

7. An apparatus according to claim 1, further comprising a power supply means for providing power to operate the apparatus.

8. An apparatus according to claim 7 wherein the power supplied to said sensor means is maintained constant and said processing means comprises means for determining a change in temperature of said sensor means in response to contact by said sensor means with a gas received thereby.

9. An apparatus according to claim 1, wherein said processing means comprises means for determining the change in the power supplied to said sensor means required to maintain said sensor means at a constant temperature when in contact with a gas received thereby.

10. An apparatus according to claim 1, wherein said standard gas has a known BTU content.

11. An apparatus according to claim 1, wherein more than one standard gas is used as a reference in calculating the BTU content of said sample gas.

12. An apparatus according to claim 1, wherein said measuring means comprises two measurement loops for measuring out precise predetermined amounts of said standard gas and of said sample gas, and said sensor means comprises two matched sensors for respectively receiving said first gas mixture and said second gas mixture and for producing simultaneous output signals in accordance therewith.

13. An apparatus according to claim 1, wherein said processing means includes a programmable microprocessor for performing data processing and for controlling operation of said apparatus.

14. An apparatus according to claim 1 wherein said sensor means comprises a wire coil incorporated in a head made of a catalyst which reacts with gases the BTU content of which is to be determined.

15. An apparatus according to claim 14 wherein said wire coil is made of platinum.

16. An apparatus according to claim 14 wherein said sensor means includes means for applying a variable voltage to said coil and means for measuring the change in said voltage necessary to maintain the temperature of said head constant when a sample gas is supplied to the sensor means.

17. An apparatus according to claim 14 wherein said sensor means includes means for supplying a constant voltage and means for measuring the change in resistance of said coil in response to a sample gas being supplied to sensor head.

18. An apparatus for measuring the BTU content of a gas sample, said apparatus comprising, a flameless catalytic sensor means for receiving a gas sample the BTU content of which is to be determined and for producing an output signal related to the BTU content of the gas sample, flow injection means for measuring out a precise predetermined amount of said sample and for diluting the sample so measured out with a carrier gas to form a mixture wherein the amount of sample is such that the sensor means operates in a diffusion limited region and said output signal is proportional to the amount of sample supplied, and signal processing means connected to said sensor means for receiving said signal and for calculating the BTU content of said sample based on said signal.

19. An apparatus according to claim 18 wherein said flow injection means comprises a measuring loop for measuring out a precise predetermined amount of gas and means for controlling filling of said loop and expulsion of the contents of the filled loop.

20. A method for measuring the BTU content of gas using a catalytic flameless sensor comprising the steps of supplying a predetermined flow of a carrier gas to said sensor, processing a signal from the sensor to establish a baseline signal, injecting a standard gas into a gas collection chamber to provide a predetermined amount of standard gas, mixing the predetermined amount of standard gas with carrier gas and supplying the mixture to said sensor, processing a signal from the sensor to produce a standard gas signal, injecting a sample gas into the gas collection chamber to provide a predetermined amount of said sample gas, mixing the predetermined amount of sample gas with carrier gas and supplying the mixture to said sensor, and processing a signal from the sensor to produce a sample gas signal indicative of the BTU content of the sample gas.

* * * * *